United States Patent
Kamijo

(10) Patent No.: US 7,110,093 B2
(45) Date of Patent: Sep. 19, 2006

(54) INSPECTION APPARATUS AND INSPECTION METHOD

(75) Inventor: Hideaki Kamijo, Saitama (JP)

(73) Assignee: Nidec Copal Corporation, Tokyo (JP)

( * ) Notice: Subject to any disclaimer, the term of this patent is extended or adjusted under 35 U.S.C. 154(b) by 413 days.

(21) Appl. No.: 10/787,216

(22) Filed: Feb. 27, 2004

(65) Prior Publication Data

US 2004/0200978 A1    Oct. 14, 2004

(30) Foreign Application Priority Data

Feb. 28, 2003  (JP)  ............................. 2003-054368
Jun. 30, 2003  (JP)  ............................. 2003-188210

(51) Int. Cl.
G06K 9/74    (2006.01)
G01J 1/32    (2006.01)

(52) U.S. Cl. ........................................ 356/71; 250/205
(58) Field of Classification Search .................. 356/71; 250/205

See application file for complete search history.

(56) References Cited

U.S. PATENT DOCUMENTS 5,915,518 A    6/1999  Hopwood et al.
5,918,960 A    7/1999  Hopwood et al.

2002/0195571 A1    12/2002  Kamijo et al.

FOREIGN PATENT DOCUMENTS

| JP | 10-40436 | 2/1998 |
|---|---|---|
| JP | 2000-132725 | 5/2000 |
| JP | 2001-307170 | 11/2001 |
| JP | 2002-074450 | 3/2002 |
| JP | 2002-109598 | 4/2002 |
| JP | 2003-006625 | 1/2003 |

*Primary Examiner*—Layla G. Lauchman
*Assistant Examiner*—Amanda Merlino
(74) *Attorney, Agent, or Firm*—Leydig, Voit & Mayer, Ltd.

(57) ABSTRACT

A banknote inspection apparatus has a conveyance path, and midway of this conveyance path there are conveyance rollers for conveying a banknote, and a fluorescence sensor for detecting a fluorescent component included in the banknote. The fluorescence sensor has a housing and in this housing there are a light-emitting device for emitting light toward a banknote, and a light-detecting device for detecting fluorescence emitted from the surface of the banknote irradiated with ultraviolet light. A fluorescent member that generates fluorescence in response to the light emitted from the light-emitting device is placed in an inspection area of the conveyance path. In inspection of the banknote, the quantity of fluorescence from the fluorescent member is first detected, and the quantity of the light emitted from the light-emitting device is corrected based on the quantity of the fluorescence detected. Then the content of the fluorescent component in the banknote is detected in that state.

7 Claims, 12 Drawing Sheets

Fig.9A

| LIGHT-SOURCE ON CURRENT (mA) | OUTPUT VOLTAGE (V) | FIRST-ORDER DIFFERENTIAL | SECOND-ORDER DIFFERENTIAL |
|---|---|---|---|
| 0 | 0.000 | | |
| 1 | 3.163 | 3.163 | |
| 2 | 4.473 | 1.310 | -1.853 |
| 3 | 5.478 | 1.005 | -0.305 |
| 4 | 6.325 | 0.847 | -0.158 |
| 5 | 7.072 | 0.747 | -0.101 |
| 6 | 7.747 | 0.675 | -0.072 |
| 7 | 8.367 | 0.621 | -0.054 |
| 8 | 8.945 | 0.578 | -0.043 |
| 9 | 9.488 | 0.543 | -0.035 |
| 10 | 10.001 | 0.513 | -0.029 |
| DETERMINATION (SLOPE OF WAVEFORM) | | | — (MINUS) |

Fig.9B

| LIGHT-SOURCE ON CURRENT (mA) | OUTPUT VOLTAGE (V) | FIRST-ORDER DIFFERENTIAL | SECOND-ORDER DIFFERENTIAL |
|---|---|---|---|
| 0 | 0.000 | | |
| 1 | 1.000 | 1.000 | |
| 2 | 2.000 | 1.000 | 0.000 |
| 3 | 3.000 | 1.000 | 0.000 |
| 4 | 4.000 | 1.000 | 0.000 |
| 5 | 5.000 | 1.000 | 0.000 |
| 6 | 6.000 | 1.000 | 0.000 |
| 7 | 7.000 | 1.000 | 0.000 |
| 8 | 8.000 | 1.000 | 0.000 |
| 9 | 9.000 | 1.000 | 0.000 |
| 10 | 10.000 | 1.000 | 0.000 |
| DETERMINATION (SLOPE OF WAVEFORM) | | | 0 (ZERO) |

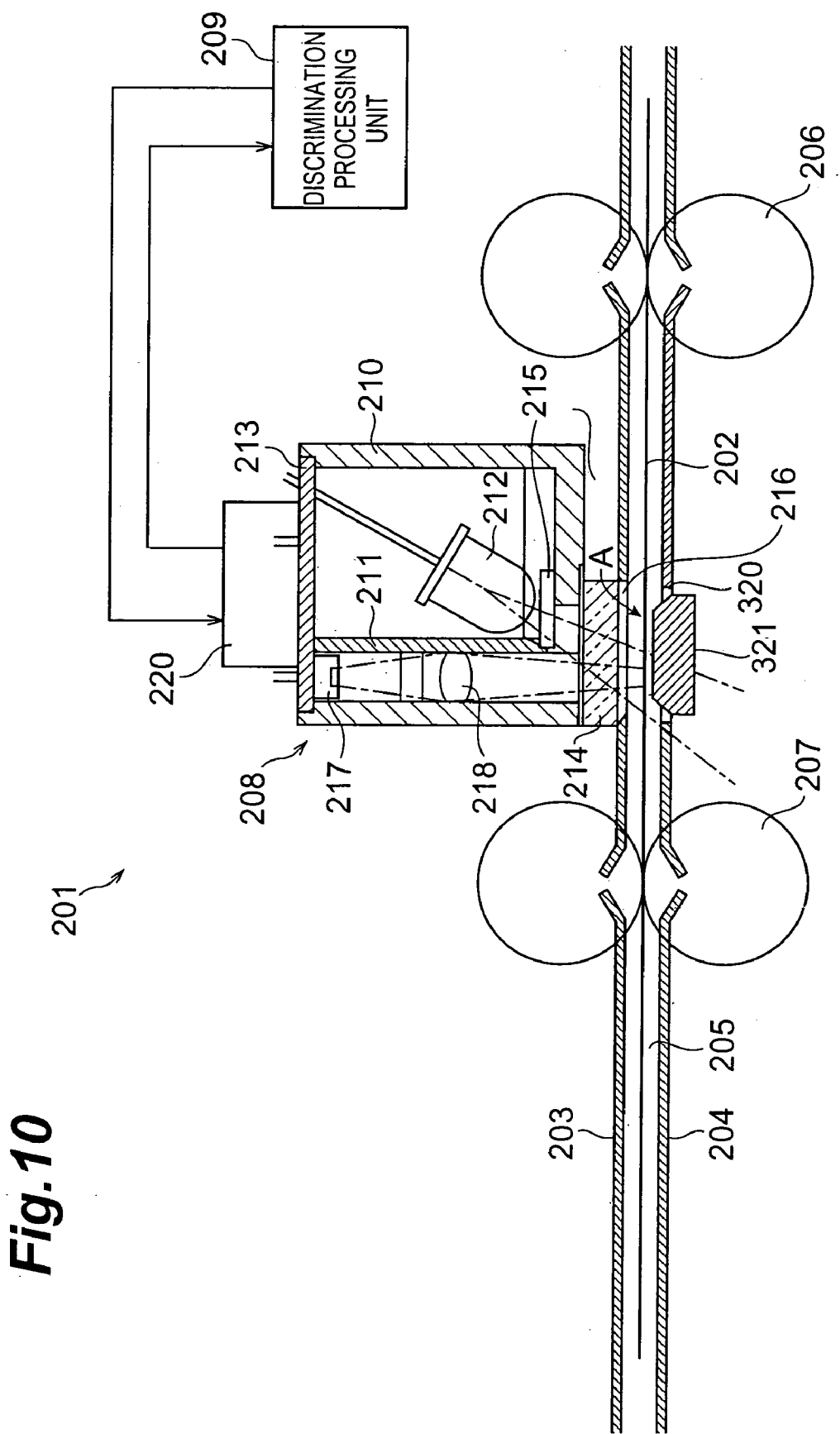

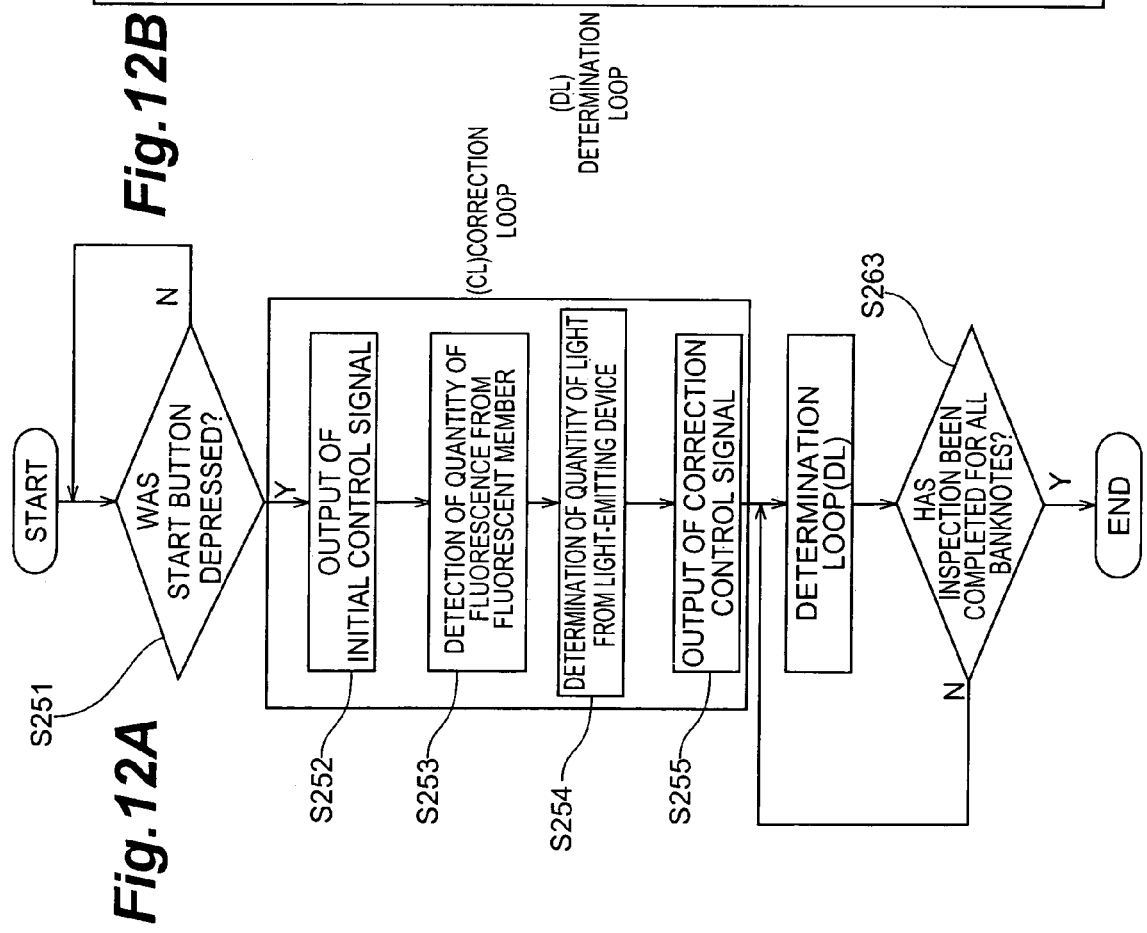

INSPECTION APPARATUS AND INSPECTION METHOD

BACKGROUND OF THE INVENTION

1. Field of the Invention

The present invention relates to inspection apparatus and method for checking the authenticity of banknotes, chits, etc., for discriminating types thereof, and so on.

2. Related Background Art

The conventional inspection apparatus for checking the authenticity of banknotes include, for example, those described in Document 1 (JP-A-9-507326) and Document 2 (JP-A-10-40436). The inspection apparatus described in these documents are configured to illuminate a banknote with ultraviolet light from a light source, measure a level of ultraviolet light reflected from the banknote, measure a quantity of fluorescence generated in the banknote, and compare the measurement levels with their respective reference levels, thereby checking the authenticity of the banknote.

SUMMARY OF THE INVENTION

However, the quantity of emission from the light source varies depending upon temperature change or the like, which can result in failure in accurately measuring the quantity of fluorescence generated in the banknote. In this case, it becomes difficult to accurately check the authenticity of banknotes and others.

An object of the present invention is to provide inspection apparatus and method capable of accurately detecting a fluorescent component included in a target object, without increase in scale of the apparatus.

An inspection apparatus of the present invention inspects a target object on the basis of a content of a fluorescent component included in the target object. This inspection apparatus comprises conveying means for conveying the target object along a conveyance path, a light-emitting device for emitting light toward the target object conveyed by the conveying means, a light-receiving device for receiving fluorescence generated by the target object as irradiated with the light, and a fluorescent member disposed on the conveyance path and adapted to generate fluorescence against the light emitted from the light-emitting device.

The inspection apparatus of this type could fail to accurately inspect the target object unless the output value of the light-receiving device (i.e., the quantity of the fluorescence generated from the target object) should be controlled in a fixed state against temperature. For this reason, the fluorescent member is located on the conveyance path as described above, and the light-receiving device receives the fluorescence generated from the fluorescent member, prior to the inspection of the target object, to detect the quantity of the fluorescence generated from the fluorescent member. A temperature characteristic of the fluorescence generated from the fluorescent member is equivalent to a temperature characteristic of the fluorescence generated from the target object containing the fluorescent component. Therefore, the quantity of emission from the light-emitting device is preliminarily corrected based on the quantity of the fluorescence generated from the fluorescent member, whereby the output value of the light-receiving device can be surely controlled to be approximately constant against temperature in the actual inspection of the target object. This permits the apparatus to accurately detect the fluorescent component in the target object, independent of temperature. Since the fluorescent member is placed on the conveyance path, the apparatus can be constructed without increase in scale.

Preferably, this inspection apparatus further comprises controlling means for, before the target object conveyed by the conveying means arrives at an inspection area of the conveyance path, receiving an output signal from the light-receiving device to detect a quantity of the fluorescence generated from the fluorescent member, and for controlling a quantity of the light from the light-emitting device on the basis of the quantity of the fluorescence generated from the fluorescent member. In this configuration, the correction process for the quantity of the light from the light-emitting device is automatically carried out based on the quantity of the fluorescence generated from the fluorescent member, prior to the arrival of the target object at the inspection area of the conveyance path, whereby the load can be reduced on an operator and others.

The fluorescent member is preferably a fluorescence glass. The fluorescence glass is a member with an ionized fluorescent medium enclosed in glass, has high environment resistance, and is unlikely to deteriorate with time. By using such a fluorescence glass, it is feasible to implement the correction for the quantity of the light from the light-emitting device on the basis of the quantity of the fluorescence generated from the fluorescent member, with a high degree of accuracy over a long period of time.

The inspection apparatus preferably comprises a light-detecting portion for outputting a signal depending on a fluorescence amount received by the light-receiving device; light source control means to control a light emitting amount from the light-emitting device for changing in analog manner to pre-determined quantity selected by the control means for controlling the quantity of the light; arithmetic means for calculating the changing fluorescence quantity; and decision means for deciding a type of the target object on the basis of the changing quantity of fluorescence.

The arithmetic means preferably calculates the changing quantity of fluorescence from the changing amount of the illumination from the light-emitting device by second order differentiating output data from the right-receiving portion.

The decision means preferably decides the type of the target object on the basis of a comparison between pre-determined quantity and changing quantity of the fluorescent.

An inspection method for inspecting a target object on the basis of a content of a fluorescent component included in the target object, the inspection method comprising steps of: detecting a start signal; calibrating a light amount from a light-emitting device; deciding a type of the target object on the basis of a fluorescent quantity from the target object illuminated by the light-emitting device; and continuing the step of deciding a type of the target object until a stop signal is detected.

The step of calibrating the light amount from the light-emitting device preferably has steps of: outputting an initial control signal to the right-emitting device; detecting a fluorescent quantity from a right-receiving device while a illuminating member is illuminated by the light-emitting device; deciding an illumination quantity for the right-emitting device by comparing between a pre-determined fluorescent quantity and the detected fluorescent quantity to the difference between these values becoming equals to zero; and outputting the illumination quantity as a corrected control signal.

The step of deciding a type of the target object preferably has steps of: changing the control signal based on the corrected signal in analog rule; calculating a second order differential of changing output from the right-receiving device; and determining a type of the target object by comparing the second order value and a pre-determined threshold value.

The present invention can be further fully understood with reference to the detailed description and accompanying drawings below. These should be considered simply as illustrative but not restrictive on the present invention.

BRIEF DESCRIPTION OF THE DRAWINGS

FIGS. 9A and 9B are tables, showing an example of results of the arithmetic-determination processing for the real banknote and counterfeit banknote shown in FIG. 8.

FIG. 10 is a sectional view showing a banknote inspection apparatus as another embodiment of the inspection apparatus.

FIGS. 12A and 12B are flowcharts showing the details of an arithmetic processing sequence of a CPU shown in FIG. 11.

DETAILED DESCRIPTION OF THE PREFERRED EMBODIMENTS

The preferred embodiments of the inspection apparatus according to the present invention will be described below in detail with reference to the drawings.

Figure 1:
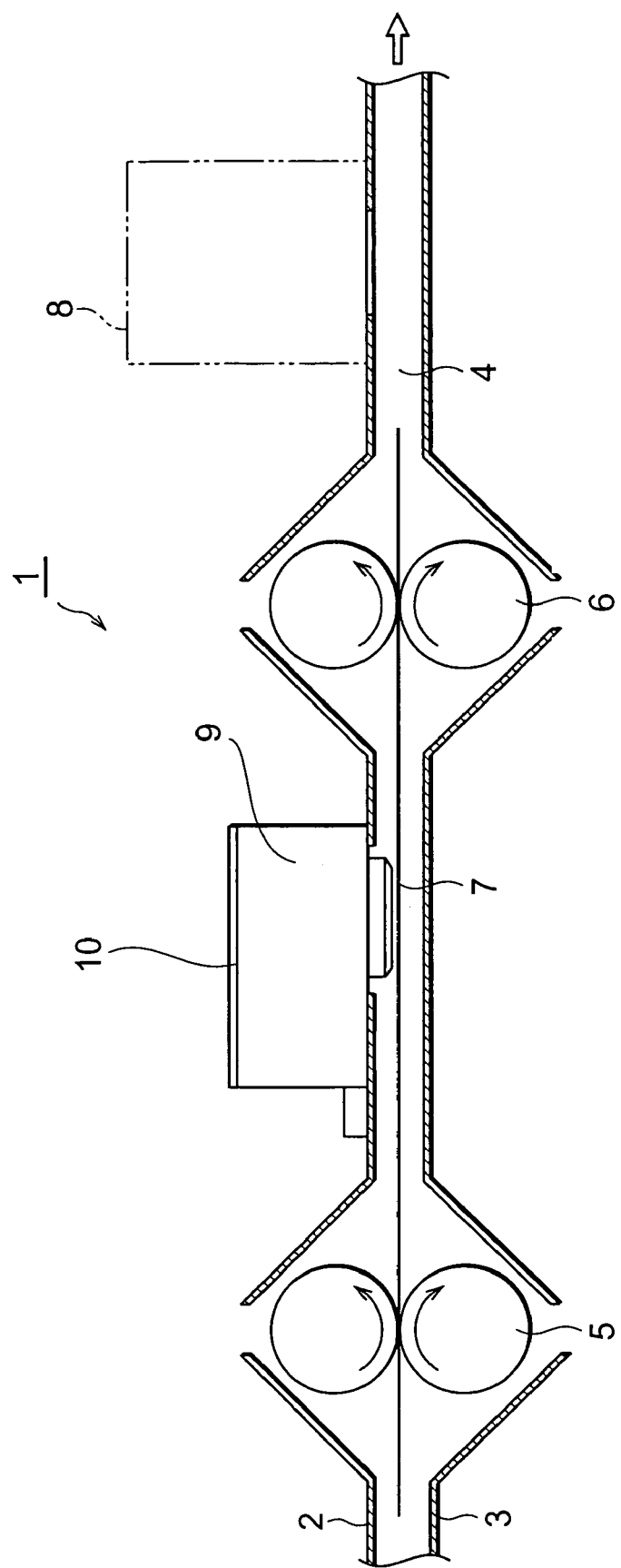
FIG. 1 is a sectional view showing a banknote inspection apparatus as an embodiment of the inspection apparatus according to the present invention.

FIG. 1 is a sectional view showing a banknote inspection apparatus as an embodiment of the inspection apparatus according to the present invention. The banknote inspection apparatus 1 is configured to check the authenticity of banknotes and determine denominations thereof. The banknote inspection apparatus 1 has a conveyance path 4 formed between an upper guide plate 2 and a lower guide plate 3. Conveyance rollers 5, 6 are placed midway on the conveyance path 4, and a banknote 7 is conveyed toward the discharge side by the conveyance rollers 5, 6.

A banknote recognizing unit 8 for discriminating a denomination of banknote 7 is placed midway on the conveyance path 4. The banknote recognizing unit 8 has a light source for illuminating the surface of banknote 7, and a CCD camera for imaging the surface of banknote 7, which are not illustrated, and is configured to collate image data from the CCD camera with given image data to determine the denomination of banknote 7.

Upstream of the banknote recognizing unit 8, there are a fluorescence sensor 9 for detecting the fluorescent component in the banknote 7, and a control unit 10 connected to this fluorescence sensor 9. These fluorescence sensor 9 and control unit 10 work to check the authenticity of the banknote, whether an authentic banknote or a forged banknote. The authenticity of banknote 7 is determined while noting that forged banknotes contain a large quantity of the fluorescent component.

Figure 2:
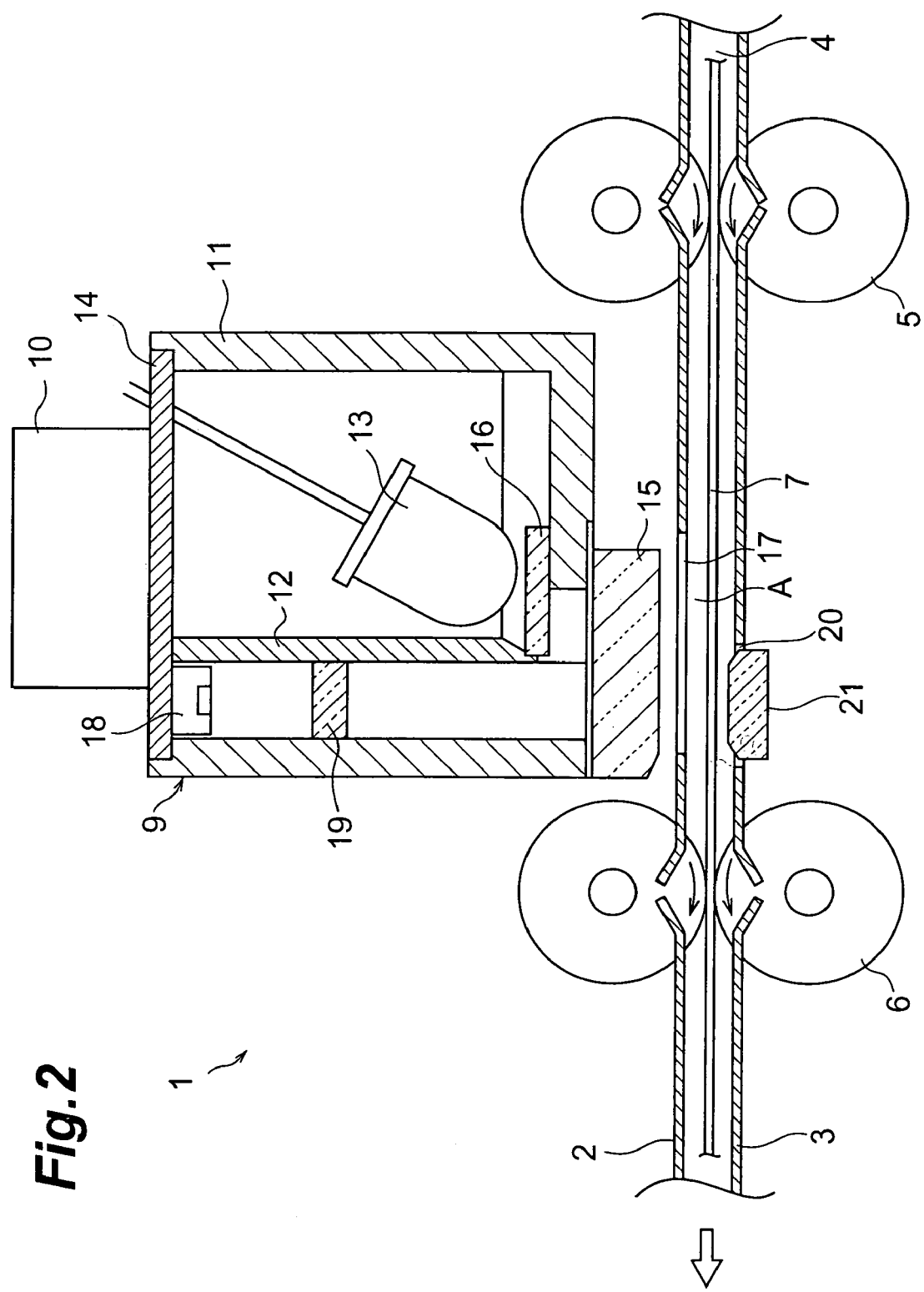
FIG. 2 is an enlarged sectional view of major part of the banknote inspection apparatus shown in FIG. 1.

The fluorescence sensor 9 has a housing 11 of nearly rectangular parallelepiped shape, as shown in FIG. 2, and a partition board 12 to divide the internal space of the housing 11 vertically is placed in the housing 11. In the housing 11, a light-emitting device (light source) 13 for emitting light toward the banknote 7 conveyed by the conveyance rollers 5, 6 is housed in one space formed by the partition board 12. This light-emitting device 13 is an ultraviolet (UV) LED for generating light containing ultraviolet components, and is fixed to a circuit board 14 provided in the upper portion of the housing 11. The reason why the LED is adopted as the light-emitting device 13 is that it has advantages of requiring only a small occupancy space even in the housing 11 being small, and demonstrating small variation in luminance and small variation in quantity of light with time.

A dust-proof glass sheet 15 is fixed to the lower surface of the housing 11 with an adhesive or the like. This dust-proof glass sheet 15 is made of quartz glass with extremely high UV transmittance, or the like. A UV transmitting filter 16 is placed between the dust-proof glass sheet 15 and the light-emitting device 13. This UV transmitting filter 16 is an optical filter that transmits only the ultraviolet components (e.g., approximately 300–400 nm) out of the light emitted from the light-emitting device 13.

The upper guide plate 2 is provided with a window 17 for letting the light from the light-emitting device 13 get out. This causes the surface of the banknote 7 to be illuminated with the light emitted from the light-emitting device. 13, on the way of conveyance of the banknote 7 by the conveyance rollers 5, 6.

In the housing 11, a light-receiving device 18 for receiving the fluorescence released from the surface of the banknote 7 under the irradiation with ultraviolet light is housed in the other space established by the partition board 12. This light-receiving device 18 is comprised of a photodiode, a phototransistor, or the like, and is fixed to the circuit board 14.

A UV cut filter 19 is placed between the dust-proof glass sheet 15 and the light-receiving device 18. This UV cut filter 19 is an optical filter for filtering out the UV components out of the light reflected on the surface of the banknote 7. The UV components in the light reflected from the banknote 7 have high energy properties, and the UV cut filter 19 removes such UV components, so as to prevent the UV components from traveling as noise into the light-receiving device 18 and causing false detection.

An aperture 20 is formed at a location of the lower guide plate 3 facing the window 17 of the upper guide plate 2, and a fluorescent member 21 to generate fluorescence against the light emitted from the light-emitting device 13 is placed in this aperture 20. This fluorescent member 21 is preferably a fluorescence glass in which an ionized fluorescent material is enclosed in glass. The fluorescence glass does not readily change with time and thus provides stable quantity of fluorescence over a long period of time. With provision of this fluorescent member 21, the fluorescence generated by the fluorescent member 21 enters the light-receiving device 18 in a state in which there is no banknote 7 in an inspection area A of the conveyance path 4.

Figure 3:
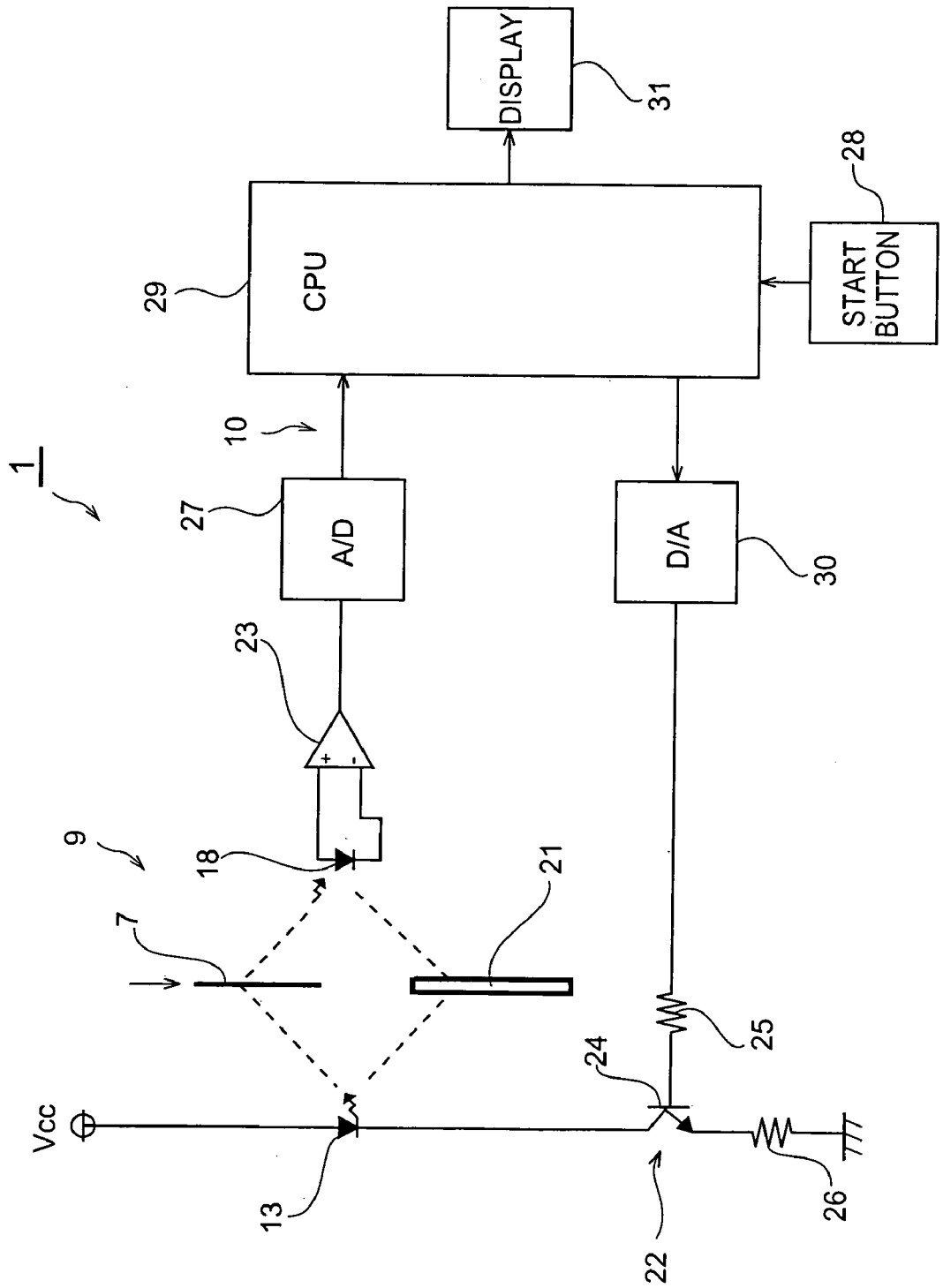
FIG. 3 is an illustration showing an electric circuit configuration of a fluorescence sensor and a block configuration of a control unit shown in FIG. 2.

FIG. 3 is an illustration showing the circuit configuration of the circuit board 14 to which the foregoing light-emitting device 13 and light-receiving device 18 are fixed, and the block configuration of the control unit 10. The circuit board 14 is provided with a drive circuit 22 connected to the light-emitting device 13, and an amplifier circuit 23 connected to the light-receiving device 18. The drive circuit 22 has a transistor 24 and resistors 25, 26, and the quantity of emission from the light-emitting device 13 is determined by a voltage supplied to this drive circuit 22. The amplifier circuit 23 converts an output from the light-receiving device 18 into a voltage signal and feeds it to the control unit 10.

The control unit 10 has an A/D converter 27, a start button 28, a CPU 29, a D/A converter 30, and a display 31. The A/D converter 27 converts an analog output signal from the amplifier circuit 23 into a digital signal. The start button 28 is a manual input means for an operator or the like to give an instruction of a start of inspection of banknote 7. The CPU 29 receives an output signal from the A/D converter 27 and an instruction signal from the start button 28 and performs predetermined arithmetic processing about the correction for the emission output quantity of the light-emitting device 13 and about the determination on the authenticity of banknote 7. The D/A converter 30 converts a digital signal from the CPU 29 into an analog signal and outputs it to the drive circuit 22. The display 31 displays information about the authenticity of the banknote 7, sent from the CPU 29, on a screen.

Figure 4:
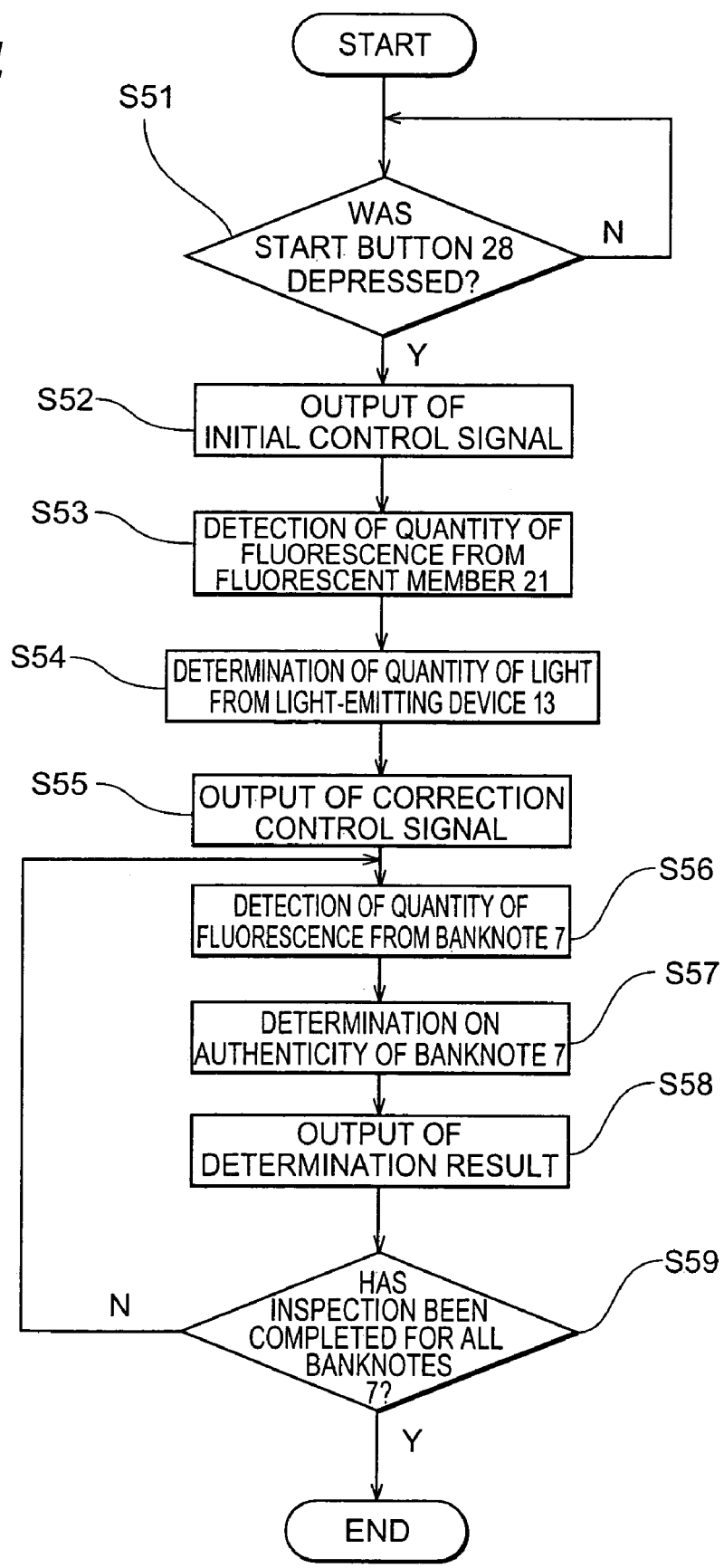
FIG. 4 is a flowchart showing the details of, an arithmetic processing sequence of a CPU shown in FIG. 3.

Now, the operation of the banknote inspection apparatus 1 will be described while elucidating the details of the arithmetic processing procedure of CPU 29, with reference to the flowchart shown in FIG. 4.

First, the operator or the like turns the start button 28 on to actuate the conveyance rollers 5, 6. A plurality of banknotes 7 are sequentially conveyed from the entrance position toward the inspection area A of the conveyance path 4.

At this time, the CPU 29 first determines whether the start button 28 was turned on (step S51) When the start button 28 is turned on, the CPU sends an initial control signal for turning the light-emitting device 13 on, to the D/A converter 30 (step S52). This results in supplying a voltage according to the initial control signal to the drive circuit 22, whereby the light-emitting device 13 emits light in a predetermined quantity.

Since no banknote 7 arrives at the inspection area A yet immediately after on of the start button 28, the fluorescent member 21 is illuminated with the light emitted from the light-emitting device 13. This causes the light-receiving device 18 to receive the fluorescence generated in the fluorescent member 21. Then an output signal from the light-receiving device 18 is fed through the A/D converter 27 to the CPU 29.

The CPU 29 detects the quantity of the fluorescence from the fluorescent member 21 on the basis of the input signal (step S53). Subsequently, the CPU determines a difference between the detected quantity of the fluorescence from the fluorescent member 21 and a preset reference fluorescence quantity, and determines such an emission quantity of light-emitting device 13 as to zero the difference (step S54). Then the CPU sends a correction control signal according to the emission quantity of light-emitting device 13 to the D/A converter 30 (step S55). This results in supplying a voltage according to the correction control signal to the drive circuit 22, and as a result, the fluorescence quantity of fluorescent member 21 is maintained at the reference fluorescence quantity.

Thereafter, a banknote 7 is conveyed into the inspection area A by the conveyance rollers 5, 6, whereupon the surface of the banknote 7 is illuminated with the light emitted from the light-emitting device 13. Where the banknote 7 contains the fluorescent component, the banknote 7 emits fluorescence and the light-receiving device 18 receives the fluorescence. Then an output signal from the light-receiving device 18 is fed through the A/D converter 27 to the CPU 29.

The CPU 29 detects the quantity of the fluorescence from the banknote 7 on the basis of the input signal (step S56). Then the CPU determines the authenticity of the banknote 7 on the basis of the detected fluorescence quantity of the banknote 7 (step S57). For example, where the banknote 7 is a counterfeit banknote, it contains the fluorescent component in large quantity, so that the detected fluorescence quantity becomes high. On the other hand, where the banknote 7 is an authentic banknote, it scarcely contains the fluorescent component, so that the detected fluorescence quantity is extremely low. Subsequently, the CPU sends the result data of the determination on the authenticity of the banknote 7 to the display 31 (step S58).

Thereafter, the CPU determines whether the determination on the authenticity has been completed for all the banknotes 7 (step S59). Before completion of the determination on the authenticity for all the banknotes 7, the processes at the above steps S56–S58 are repeatedly carried out. A decision on whether the determination on the authenticity has been completed for all the banknotes 7 is made based on a signal from a stop button (not shown) manually operated by the operator or the like, a signal from a sensor (not shown) for detecting the presence or absence of banknote 7, or the like.

Incidentally, in order to accurately perform the inspection of banknote 7, it is necessary to always control the quantity of light radiated toward the banknote 7, in a constant state for banknotes 7 of the same kind so as to keep the output from the light-receiving device 18 (the quantity of fluorescence emitted from each banknote 7) always constant. However, the emission characteristic of the light-emitting device 13 varies depending upon change in ambient temperature and upon deterioration with time, and in conjunction therewith the quantity of fluorescence emitted from the banknote 7 also varies. For this reason, if the voltage supplied to the drive circuit 22 for driving the light-emitting device 13 is always kept constant, the output from the light-receiving device 18 will differ depending upon temperature or the like, so as to result in failure in accurately determining the authenticity of banknote 7.

In contrast to it, in the present embodiment, the fluorescent member 21 as a reference for detection of fluorescence from banknote 7 is placed in the inspection area A of the conveyance path 4, the quantity of the fluorescence generated in the fluorescent member 21 is first detected, the quantity of emission from the light-emitting device 13 is corrected so as to equalize the detected value to the reference fluorescence quantity, the content of the fluorescent component in the banknote 7 is detected in that state, and the authenticity of the banknote 7 is determined based thereon. Here the fluorescence emitted from the fluorescent member 21 has the temperature characteristic equivalent to that of the fluorescence emitted from the banknote 7 containing the fluorescent component, and thus the optimal quantity correction can be made so as to fit the banknote 7. During the actual inspection of banknotes 7, therefore, the output from the light-receiving device 18 (quantity of fluorescence from banknote 7) is always kept almost constant for banknotes 7 of the same kind. This enables the apparatus to accurately detect the content of the fluorescent component in the banknote 7, is regardless of the temperature, so that the apparatus can accurately determine the authenticity of banknote 7.

Since the fluorescent member 21 is located in the aperture 20 formed in the lower guide plate 3, the banknote inspection apparatus 1 can be constructed without increase in scale.

The present invention is not limited to the above embodiment. For example, the above embodiment is directed to the detection of the fluorescent component included in the banknote 7, but the inspection target objects to which the present invention is applicable are not limited particularly to the banknotes and can be-chits, securities, cards, and so on.

According to the present invention, as detailed above, the fluorescent member to generate fluorescence against light emitted from the light-emitting device is placed on the conveyance path, whereby it is feasible to accurately detect the fluorescent component in the target object, regardless of the temperature, deterioration with time of the light-emitting device, and so on. This permits the apparatus to accurately perform the inspection of the target objects, without increase in scale.

Incidentally, since fluorescent ink included in the banknotes and others changes with time, old banknotes demonstrate lower quantity of fluorescence than new banknotes. The quantity of fluorescence also varies depending upon contamination of the banknote or the like. For this reason, in the case where, while keeping the UV irradiation quantity constant to the banknote, the quantity of fluorescence from the banknote is detected and where the determination on the authenticity of the banknote is carried out based on the detected fluorescence quantity, even a real banknote can be determined as a counterfeit banknote, depending upon the condition of the banknote.

For solving this problem, the preferred embodiment of the inspection apparatus capable of discriminating the target object with a high degree of accuracy, independent of the condition of the target object, will be described below in detail with reference to the drawings.

Figure 5:
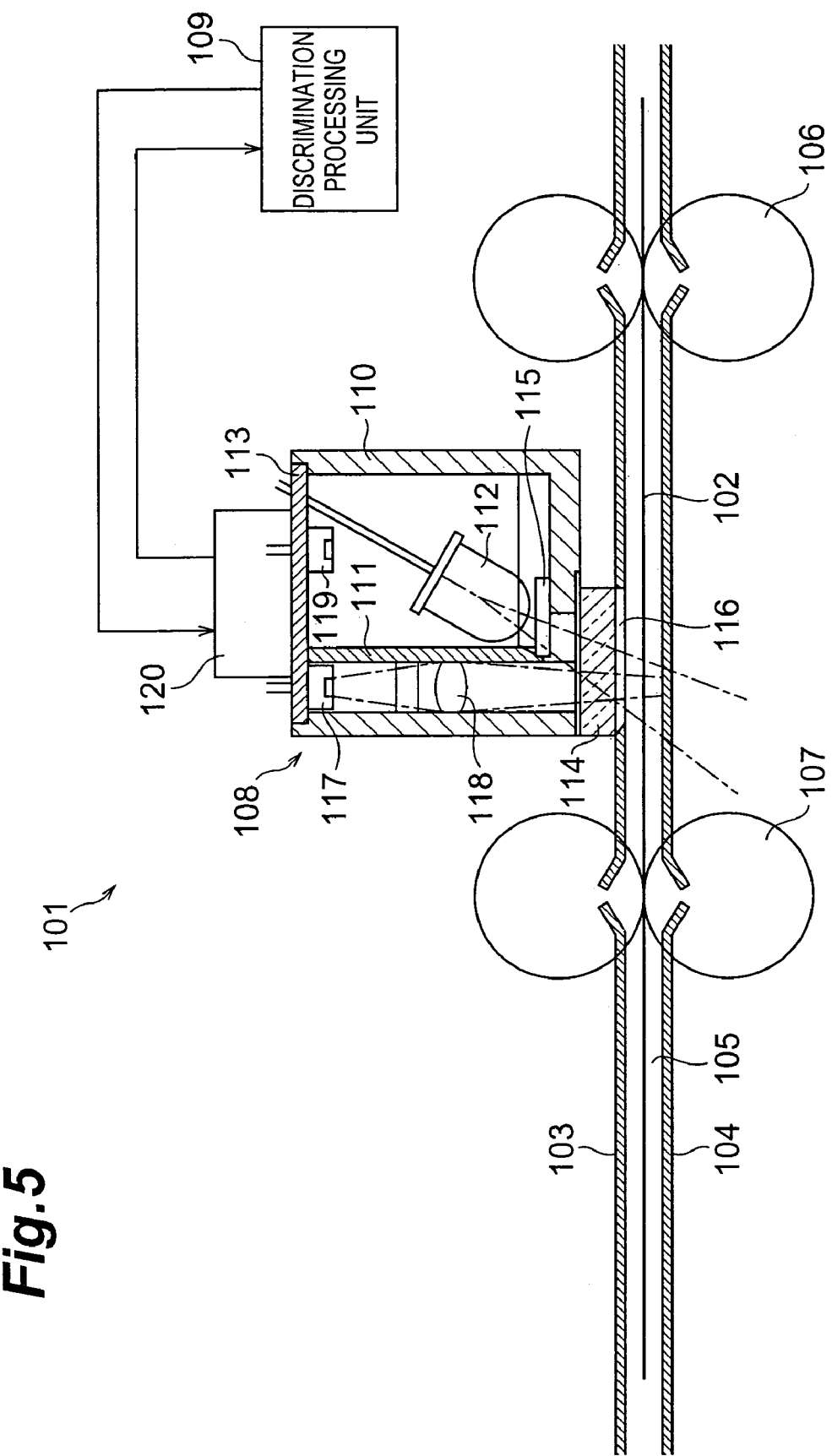
FIG. 5 is a sectional view showing a banknote inspection apparatus as another embodiment of the inspection apparatus.

FIG. 5 is a sectional view showing a banknote inspection apparatus as an embodiment of the inspection apparatus. The banknote inspection apparatus 101 of the present embodiment is an apparatus for determining the authenticity of banknote 102. The determination on the authenticity of banknote 102 is carried out, noting that counterfeit banknotes contain the fluorescent component in large quantity.

The banknote inspection apparatus 101 has a conveyance path 105 formed between an upper guide plate 103 and a lower guide plate 104. Conveyance rollers 106, 107 are placed midway on the conveyance path 105 and a banknote 102 is conveyed by the conveyance rollers 106, 107. A fluorescence sensor 108 for detecting the fluorescent component in the banknote 102 is placed between the conveyance rollers 106, 107, and a discrimination processing unit 109 is connected to this fluorescence sensor 108.

The fluorescence sensor 108 has a housing 110 of nearly rectangular parallelepiped shape and a partition board 111 extending along the direction of height is placed in this housing 110. A light source 112 for emitting light toward the banknote 102 conveyed by the conveyance rollers 106, 107 is housed in one space of the housing 110 established by the partition board 111. The light source 112 is a UV LED to generate light containing the UV components, for example, and is fixed to a printed-circuit board 113 provided in the upper portion of the housing 110.

A dust-proof glass sheet 114 is fixed to the lower surface of the housing 110. This dust-proof glass sheet 114 is made of quartz glass with extremely high UV transmittance, or the like. A UV transmitting filter 115 is placed between the dust-proof glass sheet 114 and the light source 112. This UV transmitting filter 115 is an optical filter that transmits only the UV components (e.g., approximately 300–400 nm) out of the light emitted from the light source 112.

A window 116 is provided at the location immediately below the dust-proof glass sheet 114 in the upper conveyance guide plate 103. This causes the surface of banknote 102 to be illuminated with the light emitted from the light source 112, on the way of conveyance of banknote 102 by the conveyance rollers 106, 107.

A photosensor 117 for receiving the fluorescence emitted from the surface of the banknote 102 under irradiation with UV is housed in the other space of the housing 110 established by the partition board 111. This photosensor 117 is comprised of a photodiode, a phototransistor, or the like and is fixed to the printed-circuit board 113.

A UV cut filter 118 is placed between the dust-proof glass sheet 114 and the photosensor 117. This UV cut filter 118 is an optical filter for removing the UV components out of the light reflected on the surface of the banknote 102. The UV components in the light reflected from the banknote 102 have high energy properties, and the UV cut filter 118 filters out such UV components, so as to prevent the UV components from traveling as noise into the photosensor 117 and causing false detection.

The printed-circuit board 113 is equipped with a monitor photosensor 119 for monitoring the quantity of illumination light from the light source 112 and an electronic circuit described later. Furthermore, an external connection connector 120 connected to the discrimination processing unit 109 is fixed to the printed-circuit board 113.

Figure 6:
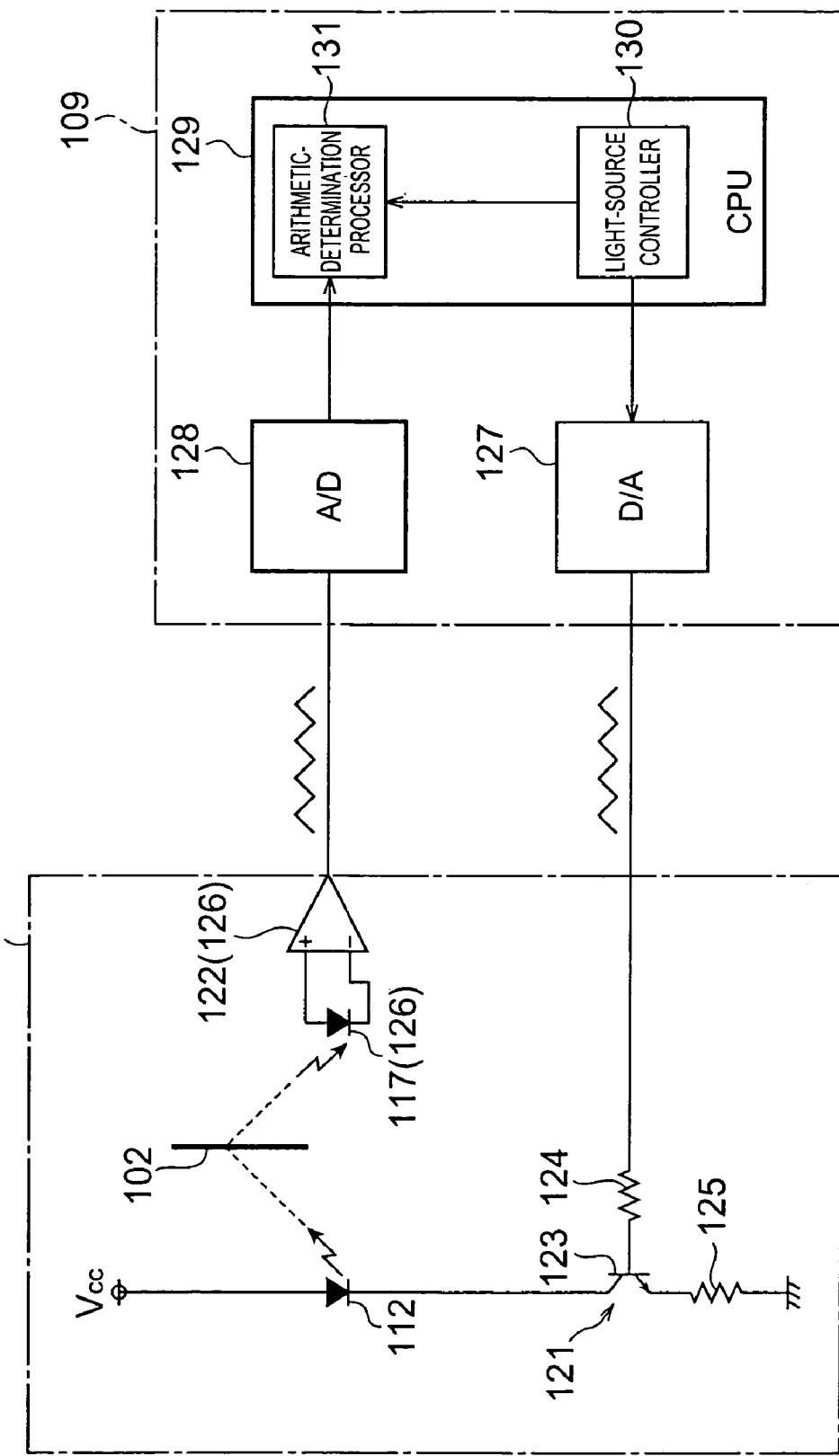
FIG. 6 is an illustration showing a circuit configuration of a printed-circuit board and functional blocks of a discrimination processing unit shown in FIG. 5.

FIG. 6 is an illustration showing the circuit configuration of the printed-circuit board 113 and the functional blocks of the discrimination processing unit 109.

In the same figure, the printed-circuit board 113 is equipped with a light-source drive circuit 121 connected to the light source 112, and an amplifier circuit 122 connected to the photosensor 117. The light-source drive circuit 121 has a transistor 123 and resistors 124, 125, and supplies a drive current according to a signal supplied from the discrimination processing unit 109, to the light source 112 to activate the light source 112. The amplifier circuit 122 converts an output from the photosensor 117 into a voltage signal and sends it to the discrimination processing unit 109. The photosensor 117 and amplifier circuit 122 constitute a fluorescence detector 126 for receiving the fluorescence emitted from the banknote 102 and for outputting a signal according to the quantity of the fluorescence.

The discrimination processing unit 109 has a D/A converter 127, an A/D converter 128, and a CPU 129. The D/A converter 127 converts a digital signal from the CPU 129 into an analog signal and outputs it to the light-source drive circuit 121. The A/D converter 128 converts an analog output signal from the amplifier circuit 122 (fluorescence detector 126) into a digital signal and outputs it to the CPU 129.

The CPU 129 has a light-source controller 130, and an arithmetic-determination processor 131. The light-source controller 130 generates and outputs light-source emission quantity data for changing the quantity of emission from the light source 112 (UV irradiation quantity) in a predetermined period in analog manner. This light-source emission quantity data is data to change the quantity of emission from the light source 112 in triangular wave shape (cf. FIG. 6), saw-tooth wave shape, sine wave shape, or the like.

The arithmetic-determination processor 131 receives output data from the A/D converter 128, calculates a variation of the fluorescence quantity of banknote 102 relative to a change of irradiation light quantity from the light source 112 (a change rate), and determines the authenticity of the banknote 102 on the basis of the result of the calculation.

The determination on the authenticity of banknote 102 will be described below with a specific example while elucidating the details of the arithmetic-determination processing procedure by the arithmetic-determination processor 131, with reference to the flowchart shown in FIG. 7.

Figure 8:
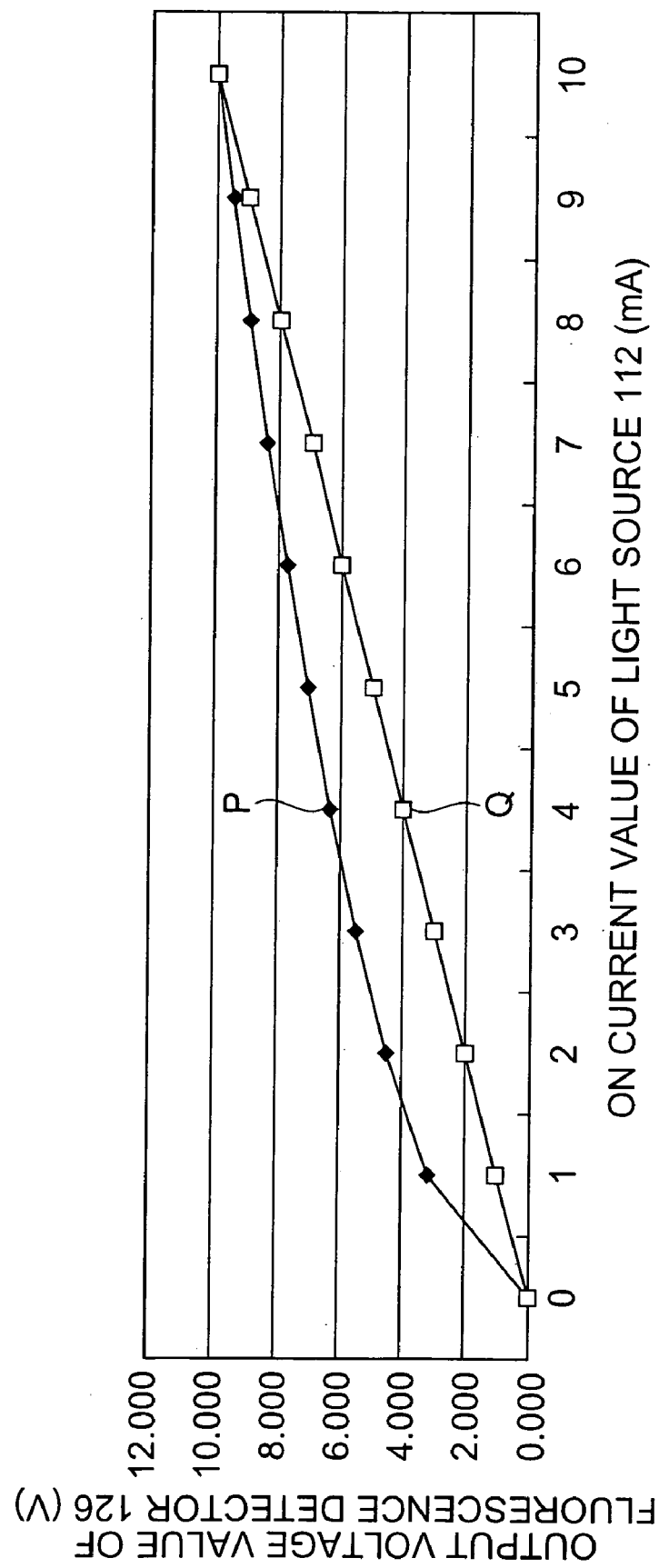
FIG. 8 is a graph showing an example of fluorescence output characteristics of banknotes against quantity of illumination light from the light source, where the banknotes, are a real banknote and a counterfeit banknote.

FIG. 8 shows an example of fluorescence output characteristics of banknotes 102 against quantity of irradiation light from the light source 112. The horizontal axis of FIG. 8 indicates on current values of the light source 112, which correspond to quantities of irradiation light from the light source 112. The vertical axis of FIG. 8 indicates output voltage values from the fluorescence detector 126, which correspond to quantities of fluorescence emitted from banknotes 102. The rhombic marks P in the figure represent data of a real banknote containing an extremely small amount of the fluorescent component, and have a quadratic curve characteristic. The square marks Q in the figure represent data of a counterfeit banknote such as copy paper or the like containing a large amount of the fluorescent component, and have a linear characteristic. These characteristics are maintained regardless of whether the banknote is old, whether the banknote is contaminated, and so on.

Figure 7:
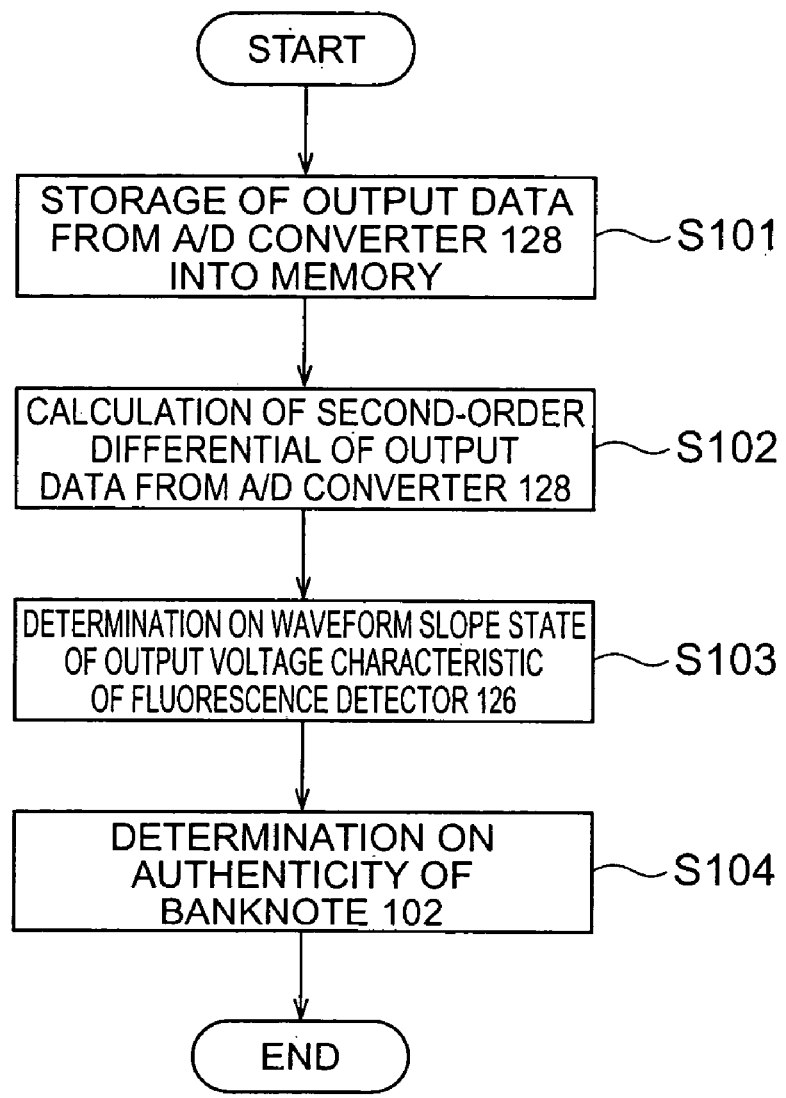
FIG. 7 is a flowchart showing the details of an arithmetic and determination processing sequence carried out by an arithmetic-determination processor shown in FIG. 6.

In executing the arithmetic-determination processing by the arithmetic-determination processor 131, the output data from the A/D converter 128 is first stored into a memory (not shown) (step S101 in FIG. 7). The output data from the A/D converter 128 is fluorescence quantity detection data corresponding to the light-source emission quantity generated in the light-source controller 130.

Subsequently, the processor calculates a second-order differential of the fluorescence quantity detection data with respect to the light-source emission quantity data (step S102 in FIG. 7). This results in calculating a change amount of the fluorescence quantity of the banknote 102 relative to a change of quantity of irradiation light from the light source 112. At this time, differential values of fluorescence quantity detection data D are calculated as follows.

First-order differential: $D_{n+1} - D_n$

Second-order differential: $(D_{n+1} - D_n) - (D_n - D_{n-1})$

First-order differential and second-order differential values of each fluorescence quantity detection data of the real banknote indicated by the rhombic marks P in FIG. 8 are presented in FIG. 9A, and first-order differential and second-order differential values of each fluorescence quantity detection data of the counterfeit banknote indicated by the square marks Q in FIG. 8 are presented in FIG. 9B.

Subsequently, the processor determines a waveform slope state of the output voltage characteristic of the fluorescence detector 126 against quantity of irradiation light from the light source 112, from the second-order differential values determined as described above (step S103 in FIG. 7). This waveform slope state is selected from three states of "minus (−)," "zero (0)," and "plus (+)."

Specifically, for determining the waveform slope state, for example, the processor calculates an average of the second-order differential values and compares it with preset determination thresholds. When the average of the second-order differential values is larger than a negative determination threshold and smaller than a positive determination threshold, the processor determines that the sign of the waveform slope state is "zero." When the average of the second-order differential values is smaller than the negative determination threshold, the processor determines that the sign of the waveform slope state is "minus." When the average of the second-order differential values is larger than the positive determination threshold, the processor determines that the sign of the waveform slope state is "plus." For determining the waveform slope state, it is also possible to adopt any other technique, e.g., a method of comparing a minimum or a maximum of the second-order differential values with determination thresholds or the like, instead of the average of the second-order differential values as described above.

When the second-order differential values of the calculation data shown in FIGS. 9A and 9B are compared with the predetermined determination thresholds, the sign of the waveform slope state of the real banknote shown in FIG. 9A is determined to be "minus," whereas that of the counterfeit banknote shown in FIG. 9B "zero."

Subsequently, the processor determines the quality of the banknote 102 from the waveform slope state determined as described above, to determine the authenticity of the banknote 102 (step S104 in FIG. 7). Specifically, when the sign of the waveform slope state is "minus," the processor determines that the banknote 102 scarcely contains the fluorescent component and thus that the banknote 102 is an authentic banknote. When the sign of the waveform slope state is "zero," the processor determines that the banknote 102 contains a large amount of the fluorescent component and thus that the banknote 102 is a counterfeit. Furthermore, when the sign of the waveform slope state is "plus," the processor determines that the banknote 102 has the other quality of paper and thus also determines in this case that the banknote 102 is a counterfeit.

Therefore, the banknote shown in FIG. 9A is determined to be a real banknote, because the sign of the waveform slope state is "minus." In contrast, the banknote shown in FIG. 9B is determined to be a counterfeit, because the sign of the waveform slope state is "zero."

In the configuration above, the light-source drive circuit 121, D/A converter 127, and the light-source controller 130 of the CPU 129 constitute a light-source emission quantity controlling means for controlling the light source 112 so as to change the quantity of irradiation light from the light source 112 in analog manner. The steps S101, S102 by the A/D converter 128 and the arithmetic-determination processor 131 of the CPU 129 constitute an arithmetic means for receiving the output signal from the fluorescence detector 126 and calculating the change amount of the fluorescence quantity against change of quantity of irradiation light from the light source 112. The steps S103, S104 by the arithmetic-determination processor 131 of the CPU 129 constitute a discriminating means for discriminating the target object 102 on the basis of the change amount of the fluorescence quantity calculated by the arithmetic means.

Incidentally, the banknotes contain a trace of the fluorescent material and the amount of the fluorescent material varies with time; therefore, the quantity of fluorescence from new banknotes is different from that from worn-out banknotes. The quantity of fluorescence also differs depending upon contamination of the banknote or the like.

In this respect, instead of determining the authenticity of the banknote 102 on the basis of the quantity of the fluorescence from the banknote 102, the present embodiment is configured to calculate the change amount of the fluorescence quantity of the banknote 102 against change of quantity of irradiation light from the light source 112 and determine the authenticity of the banknote 102 on the basis of the change amount of the fluorescence quantity. Change amounts of fluorescence quantity of banknotes 102 are almost constant, independent of states of banknotes 102 (whether the banknote is old or not, whether there is contamination or not, etc.). Accordingly, it becomes feasible to determine the authenticity with a high degree of accuracy, almost free of influence of the state of banknote 102.

The inspection apparatus is not limited to the above embodiment. For example, the above embodiment is configured to inspect the banknotes, but, without having to be limited particularly to the banknotes, the apparatus can also be applied to such inspection target objects as chits, securities, cards, and so on.

The following invention can be extracted from the banknote inspection apparatus 101 described above with reference to FIGS. 5 to 9A, 9B.

Namely, the invention provides an inspection apparatus for inspecting a target object on the basis of the content of the fluorescent component included in the target object. This inspection apparatus comprises a light source for emitting light toward the target object; a fluorescence detector for receiving fluorescence emitted from the target object and outputting a signal according to the quantity of the fluorescence; light-source emission quantity controlling means for controlling the light source so as to change the quantity of irradiation light from the light source in analog manner; arithmetic means for receiving an output signal from the fluorescence detector and calculating a change amount of the fluorescence quantity against a change of the quantity of irradiation light from the light source; and discriminating means for discriminating the target object on the basis of the change amount of fluorescence quantity calculated by the arithmetic means.

In general, a fluorescent material has such an output characteristic as to change the quantity of generated fluorescence against change of quantity of irradiation light. While the quantity of fluorescence from the fluorescent material decreases because of deterioration with time, the output characteristic of the fluorescent material is maintained. The present inspection apparatus was achieved in view of this point. Namely, when the light source is controlled so as to change the quantity of irradiation light from the light source in analog manner, the quantity of fluorescence emitted from the target object also varies in analog manner according to the change in the quantity of irradiation light from the light source, and the fluorescence detector detects it. Then the arithmetic means calculates the change amount of the fluorescence quantity relative to the change of quantity of irradiation light from the light source. Here, a target object containing the fluorescent component has the fluorescence output characteristic almost linearly changing against quantity of irradiation light from the light source, whereas a target object scarcely containing the fluorescent component has the fluorescence output characteristic changing like a quadratic curve against quantity of irradiation light from the light source. Therefore, they exhibit completely different change amounts of fluorescence quantity against change of quantity of irradiation light from the light source. Even if the fluorescent material in the target object experiences deterioration with time or the like, there is little variation in the change amount of the fluorescence quantity against quantity of irradiation light from the light source. Therefore, by discriminating the target object on the basis of the change amount of fluorescence quantity as described above, it becomes feasible to determine the authenticity of the target object or the like with a high degree of accuracy, independent of the state of the target object.

Here the arithmetic means is preferably configured to calculate the change amount of fluorescence quantity against change of quantity of irradiation light from the light source, based on the second-order differential of the output signal data from the fluorescence detector. In this case, the change amount of fluorescence quantity against change of quantity of irradiation light from the light source can be surely gained by the simple arithmetic processing.

The discriminating means is preferably configured to compare the change amount of fluorescence quantity with a preset determination threshold and discriminate the target object on the basis of the result of the comparison. In this case, by properly changing the determination threshold, it becomes feasible to perform the discrimination of the target object with a higher degree of accuracy.

Since the inspection apparatus comprises the light-source emission quantity controlling means for controlling the light source so as to change the quantity of irradiation light from the light source in analog manner; the arithmetic means for receiving the output signal from the fluorescence detector and calculating the change amount of the fluorescence quantity against change of quantity of irradiation light from the light source; and the discriminating means for discriminating the target object on the basis of the change amount of fluorescence quantity calculated by the arithmetic means, it can discriminate the target object with a high degree of accuracy, regardless of the state of the target object.

Next, another embodiment of a banknote inspection apparatus according to the present invention is explained. FIG. 10 is a sectional view showing a banknote inspection apparatus as best mode embodiment of the inspection apparatus. The banknote inspection apparatus 201 of the present embodiment is an apparatus for determining the authenticity of banknote 202. The determination on the authenticity of banknote 202 is carried out, noting that counterfeit banknotes contain the fluorescent component in large quantity.

The banknote inspection apparatus 201 has a conveyance path 205 formed between an upper guide plate 203 and a lower guide plate 204. Conveyance rollers 206, 207 are placed midway on the conveyance path 205 and a banknote 202 is conveyed by the conveyance rollers 206, 207. A fluorescence sensor 208 for detecting the fluorescent component in the banknote 202 is placed between the conveyance rollers 206, 207, and a discrimination processing unit 209 is connected to this fluorescence sensor 208.

The fluorescence sensor 208 has a housing 210 of nearly rectangular parallelepiped shape and a partition board 211 extending along the direction of height is placed in this housing 210. A light source 212 for emitting light toward the banknote 202 conveyed by the conveyance rollers 206, 207 is housed in one space of the housing 210 established by the partition board 211. The light source 212 is a UV LED to generate light containing the UV components, for example, and is fixed to a printed-circuit board 213 provided in the upper portion of the housing 210.

A dust-proof glass sheet 214 is fixed to the lower surface of the housing 210. This dust-proof glass sheet 214 is made of quartz glass with extremely high UV transmittance, or the like. A UV transmitting filter 215 is placed between the dust-proof glass sheet 214 and the light source 212. This UV transmitting filter 215 is an optical filter that transmits only the UV components (e.g., approximately 300–400 nm) out of the light emitted from the light source 212.

An aperture 320 is formed at a location of the lower guide plate 204 facing the window 216 of the upper guide plate 203, and a fluorescent member 321 to generate fluorescence against the light emitted from the light-emitting device 212 is placed in this aperture 320. This fluorescent member 321 is preferably a fluorescence glass in which an ionized fluorescent material is enclosed in glass. The fluorescence glass does not readily change with time and thus provides stable quantity of fluorescence over a long period of time. With provision of this fluorescent member 321, the fluorescence generated by the fluorescent member 321 enters the light-receiving device 217 in a state in which there is no banknote 202 in an inspection area A of the conveyance path 205.

A window 216 is provided at the location immediately below the dust-proof glass sheet 214 in the upper guide plate 203. This causes the surface of banknote 202 to be illuminated with the light emitted from the light source 212, on the way of conveyance of banknote 202 by the conveyance rollers 206, 207.

A photosensor 217 for receiving the fluorescence emitted from the surface of the banknote 202 under irradiation with UV is housed in the other space of the housing 210 established by the partition board 211. This photosensor 217 is comprised of a photodiode, a phototransistor, or the like and is fixed to the printed-circuit board 213.

A UV cut filter 218 is placed between the dust-proof glass sheet 214 and the photosensor 217. This UV cut filter 218 is an optical filter for removing the UV components out of the light reflected on the surface of the banknote 202. The UV components in the light reflected from the banknote 202 have high energy properties, and the UV cut filter 218 filters out such UV components, so as to prevent the UV components from traveling as noise into the photosensor 217 and causing false detection.

The printed-circuit board 213 is equipped with an electronic circuit described later. Furthermore, an external connection connector 220 connected to the discrimination processing unit 209 is fixed to the printed-circuit board 213.

Figure 11:
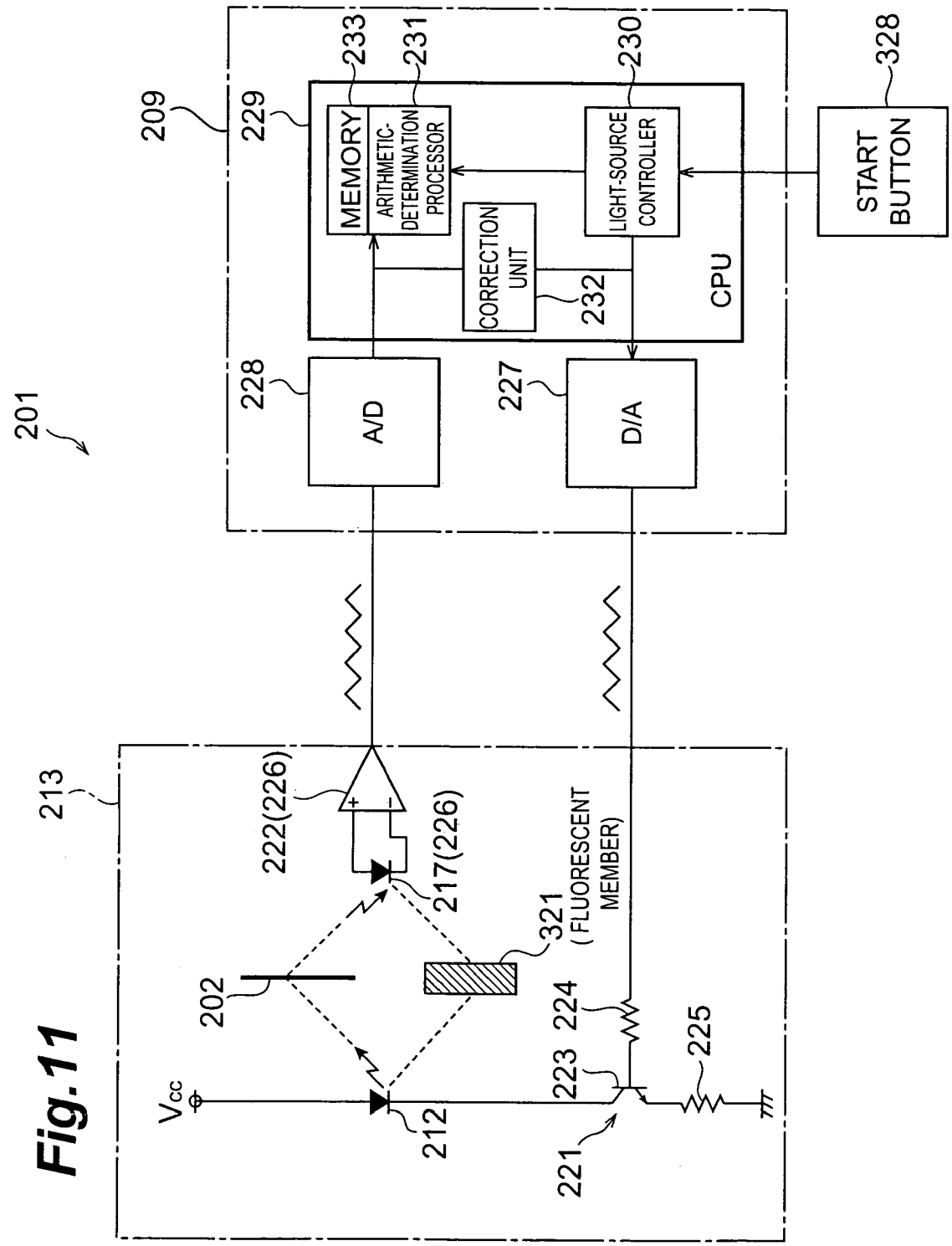
FIG. 11 is an illustration showing a circuit configuration of a printed-circuit board and functional blocks of a discrimination processing unit shown in FIG. 10.

FIG. 11 is an illustration showing the circuit configuration of the printed-circuit board 213 and the functional blocks of the discrimination processing unit 209.

In the same figure, the printed-circuit board 213 is equipped with a light-source drive circuit 221 connected to the light source 212, and an amplifier circuit 222 connected to the photosensor 217. The light-source drive circuit 221 has a transistor 223 and resistors 224, 225, and supplies a drive current according to a signal supplied from the discrimination processing unit 209, to the light source-212 to activate the light source 212. The amplifier circuit 222 converts an output from the photosensor 217 into a voltage signal and sends it to the discrimination processing unit 209. The photosensor 217 and amplifier circuit 222 constitute a fluorescence detector 226 for receiving the fluorescence emitted from the banknote 202 and for outputting a signal according to the quantity of the fluorescence.

The discrimination processing unit 209 has a D/A converter 227, an A/D converter 228, and a CPU 229. The D/A converter 227 converts a digital signal from the CPU 229 into an analog signal and outputs it to the light-source drive circuit 221. The A/D converter 228 converts an analog output signal from the amplifier circuit 222 (fluorescence detector 226) into a digital signal and outputs it to the CPU 229.

The CPU 229 has a light-source controller 230, an arithmetic-determination processor 231, a correction-unit 232 and memory 233. The light-source controller 230 generates and outputs light-source emission quantity data for changing the quantity of emission from the light source 212 (UV irradiation quantity) in a predetermined period in analog manner. This light-source emission quantity data is data to change the quantity of emission from the light source 212 in triangular wave shape (cf. FIG. 11), saw-tooth wave shape, sine wave shape, or the like.

The correction unit 232 calibrate the quantity of emission from the light emitting device 212 based on the emission from the fluorescent member 312. Hereinafter, these procedure is mentioned as correction loop (CL). In the next procedure, a data from the A/D converter 228 while the banknote inspection is stored in the memory 233. These following procedures for banknote authenticity determination is mentioned as decision loop (DL) after all.

The arithmetic-determination processor 231 receives output data from the A/D converter 228, calculates a variation of the fluorescence quantity of banknote 202 relative to a change of irradiation light quantity from the light source 212 (a change rate), and determines the authenticity of the banknote 202 on the basis of the result of the calculation.

The correction for the emission from the light emitting device 212 by the correction means (correction unit 232) (correction loop) and the determination on the authenticity of banknote 202 (determination loop) will be described below with a specific example while elucidating the details of the arithmetic-determination processing procedure by the arithmetic-determination processor 231, with reference to the flowchart shown in FIGS. 12A and 12B.

The CPU 229 first determines whether the start button 328 was turned on (step S251). When the start button 328 is turned on, the light source controller 230 sends an initial control signal for turning the light-emitting device 212 on, to the D/A converter 227 (step S252). This results in supplying a voltage according to the initial control signal to the drive circuit 221, whereby the light-emitting device 212 emits light in a predetermined quantity.

Since no banknote 202 arrives at the inspection area A yet immediately after on of the start button 328, the fluorescent member 321 is illuminated with the light emitted from the light-emitting device 212. This causes the light-receiving device 217 to receive the fluorescence generated in the fluorescent member 321. Then an output signal from the light-receiving device 217 is fed through the A/D converter 228 to the correction unit 232 in the CPU 229.

The correction unit 232 detects the quantity of the fluorescence from the fluorescent member 321 on the basis of the input signal (step S253). Subsequently, the unit determines a difference between the detected quantity of the fluorescence from the fluorescent member 321 and a preset reference fluorescence quantity, and determines such an emission quantity of light-emitting device 212 as to zero the difference (step S254). Then the unit sends a correction control signal according to the emission quantity of light-emitting device 212 to the D/A converter 227 (step S255). This results in supplying a voltage according to the correction control signal to the drive circuit 222, and as a result, the fluorescence quantity of fluorescent member 321 is maintained at the reference fluorescence quantity.

The procedures processed in the correction unit 232 corresponds to steps from S252 to S255 as correction loop (CL). After the correction loop, the determination loop (DL) is carried out. In the determination loop, an output signal is decided based on the calibrated control signal, and the output signal is changed with analog manner (phased step value) while the inspection (step S256 in FIG. 12B). The emission from the light-emitting device 212 based on the phased output signal is detected by the light-receiving device 217 and fed to the A/D converter 228 for banknote authenticity determination (step S257 in FIG. 12B).

In executing the arithmetic-determination processing by the arithmetic-determination processor 231, the output data from the A/D converter 228 is first stored into a memory 233 (step S258 in FIG. 12B). The output data from the A/D converter 228 is fluorescence quantity detection data corresponding to the light-source emission quantity generated in the light-source controller 230.

Subsequently, the processor calculates a second-order differential of the fluorescence quantity detection data with respect to the light-source emission quantity data (step S259 in FIG. 12B). This results in calculating a change amount of the fluorescence quantity of the banknote 202 relative to a change of quantity of irradiation light from the light source 212. At this time, differential values of fluorescence quantity detection data D are calculated as follows.

First-order differential: $D_{n+1}-D_n$

Second-order differential: $(D_{n+1}-D_n)-(D_n-D_{n-1})$

Subsequently, the processor determines a waveform slope state of the output voltage characteristic of the fluorescence detector 226 against quantity of irradiation light from the light source 212, from the second-order differential values determined as described above (step S260 in FIG. 12B) This waveform slope state is selected from three states of "minus (−)," "zero (0)," and "plus (+)."

Specifically, for determining the waveform slope state, for example, the processor calculates an average of the second-order differential values and compares it with preset determination thresholds. When the average of the second-order differential values is larger than a negative determination threshold and smaller than a positive determination threshold, the processor determines that the sign of the waveform slope state is "zero." When the average of the second-order differential values is smaller than the negative determination threshold, the processor determines that the sign of the waveform slope state is "minus." When the average of the second-order differential values is larger than the positive determination threshold, the processor determines that the sign of the waveform slope state is "plus." For determining the waveform slope state, it is also possible to adopt any other technique, e.g., a method of comparing a minimum or a maximum of the second-order differential values with determination thresholds or the like, instead of the average of the second-order differential values as described above.

Subsequently, the processor determines the quality of the banknote 202 from the waveform slope state determined as described above, to determine the authenticity of the banknote 202 (step S261 in FIG. 12B). Specifically, when the sign of the waveform slope state is "minus," the processor determines that the banknote 202 scarcely contains the fluorescent component and thus that the banknote 202 is an authentic banknote. When the sign of the waveform slope state is "zero," the processor determines that the banknote 202 contains a large amount of the fluorescent component and thus that the banknote 202 is a counterfeit. Furthermore, when the sign of the waveform slope state is "plus," the processor determines that the banknote 202 has the other quality of paper and thus also determines in this case that the banknote 202 is a counterfeit. Then the processor outputs the determination result (step S262 in FIG. 12B).

These described determination loop (DL) corresponds to the steps from S256 to S262 described in FIG. 12B.

Thereafter, the CPU determines whether the determination on the authenticity has been completed for all the banknotes 202 (step S263 in FIG. 12A) Before completion of the determination on the authenticity for all the banknotes 202, the processes at the above steps S256–S262 are repeatedly carried out. A decision on whether the determination on the authenticity has been completed for all the banknotes 202 is made based on a signal from a stop button (not shown) manually operated by the operator or the like, a signal from a sensor (not shown) for detecting the presence or absence of banknote 202, or the like.

In the above, correction means 232 for calibrating the emission from the light-emitting device and decision means 231 for deciding the authenticity of the banknote are described separately. However, the embodiment is not restricted by this example. For instance, even while the banknote inspection, the correction loop can be carried out, if there is a distance between banknotes. In this case, there is another advantage that long period precisely inspection is available with no affection from the fluctuation of environment temperature.

In the present embodiment, the fluorescent member 321 as a reference for detection of fluorescence from banknote 202 is placed in the inspection area A of the conveyance path 205, the quantity of the fluorescence generated in the fluorescent member 321 is first detected, the quantity of emission from the light-emitting device 212 is corrected so as to equalize the detected value to the reference fluorescence quantity, the content of the fluorescent component in the banknote 202 is detected in that state, and the authenticity of the banknote 202 is determined based thereon. Here the fluorescence emitted from the fluorescent member 321 has the temperature characteristic equivalent to that of the fluorescence emitted from the banknote 202 containing the fluorescent component, and thus the optimal quantity correction can be made so as to fit the banknote 202. During the actual inspection of banknotes 202, therefore, the output from the light-receiving device 217 (quantity of fluorescence from banknote 202) is always kept almost constant for banknotes 202 of the same kind. This enables the apparatus to accurately detect the content of the fluorescent component in the banknote 202, regardless of the temperature, so that the apparatus can accurately determine the authenticity of banknote 202.

Since the fluorescent member 321 is located in the aperture 320 formed in the lower guide plate 204, the banknote inspection apparatus 201 can be constructed without increase in scale.

Further, a fluorescent material has such an output characteristic as to change the quantity of generated fluorescence against change of quantity of irradiation light. While the quantity of fluorescence from the fluorescent material decreases because of deterioration with time, the output characteristic of the fluorescent material is maintained. The present inspection apparatus was achieved in view of this point. Namely, when the light source is controlled so as to change the quantity of irradiation light from the light source in analog manner, the quantity of fluorescence emitted from the target object also varies in analog manner according to the change in the quantity of irradiation light from the light source, and the fluorescence detector detects it. Then the arithmetic means calculates the change amount of the fluorescence quantity relative to the change of quantity of irradiation light from the light source. Here, a target object containing the fluorescent component has the fluorescence output characteristic almost linearly changing against quantity of irradiation light from the light source, whereas a target object scarcely containing the fluorescent component has the fluorescence output characteristic changing like a quadratic curve against quantity of irradiation light from the light source. Therefore, they exhibit completely different change amounts of fluorescence quantity against change of quantity of irradiation light from the light source. Even if the fluorescent material in the target object experiences deterioration with time or the like, there is little variation in the change amount of the fluorescence quantity against quantity of irradiation light from the light source. Therefore, by discriminating the target object on the basis of the change amount of fluorescence quantity as described above, it becomes feasible to determine the authenticity of the target object or the like with a high degree of accuracy, independent of the state of the target object.

Moreover, the arithmetic means is configured to calculate the change amount of fluorescence quantity against change of quantity of irradiation light from the light source, based on the second-order differential of the output signal data from the fluorescence detector. By this method, the change amount of fluorescence quantity against change of quantity of irradiation light from the light source can be surely gained by the simple arithmetic processing.

The discriminating means is preferably configured to compare the change amount of fluorescence quantity with a preset determination threshold and discriminate the target object on the basis of the result of the comparison. In this case, by properly changing the determination threshold, it becomes feasible to perform the discrimination of the target object with a higher degree of accuracy.

According to the present invention, as detailed above, the fluorescent member to generate fluorescence against light emitted from the light-emitting device to calibrate the light-emitting device is placed on the conveyance path, whereby it is feasible to accurately detect the fluorescent component in the target object, regardless of the temperature, deterioration with time of the light-emitting device, and so on. This permits the apparatus to accurately perform the inspection of the target objects, without increase in scale.

Moreover, while the inspection of the banknote the inspection apparatus comprises the light-source emission quantity controlling means for controlling the light source so as to change the quantity of irradiation light from the light source in analog manner; the arithmetic means for receiving the output signal from the fluorescence detector and calculating the change amount of the fluorescence quantity against change of quantity of irradiation light from the light source; and the discriminating means for discriminating the target object on the basis of the change amount of fluorescence quantity calculated by the arithmetic means, it can discriminate the target object with a high degree of accuracy, regardless of the state of the target object.

In addition, by calibrating the emission from the light-emitting device while the inspection, the object is inspected in long period with not affected from environment temperature fluctuation.

It is apparent from the above description of the present invention that the present invention can be modified in various ways. The present invention embraces such modifications, without departing from the spirit and scope of the present invention, and all improvements obvious to those skilled in the art should be considered to be included in the scope of the claims which follow.

What is claimed is:

1. An inspection apparatus for inspecting a target object based on content of a fluorescent component included in the target object, the inspection apparatus comprising:
   conveying means for conveying the target object along a conveyance path;
   a light-emitting device for emitting light toward the target object conveyed by the conveying means;
   a light-detecting device for detecting fluorescence emitted from the target object when irradiated with the light;
   a fluorescent member disposed on the conveyance path for generating fluorescence in response to light emitted from the light-emitting device: and
   controlling means for, before the target object conveyed by the conveying means arrives at an inspection area of the conveyance path, receiving an output signal from the light-detecting device to detect quantity of the fluorescence generated from the fluorescent member, and for controlling quantity of the light from the light-emitting device based on quantity of the fluorescence generated by the fluorescent member.

2. The inspection apparatus according to claim 1, wherein the fluorescent member is a fluorescence glass.

3. The inspection apparatus according to claim 1, further comprising:
   a light-detecting portion for outputting a signal depending on quantity of the fluorescence detected by the light-detecting device;
   light source control means for controlling quantity of light emitted from the light-emitting device and for changing, in an analog manner, to a pre-determined quantity of light selected by the light source control means for controlling the quantity of the light emitted;
   arithmetic means for calculating changing fluorescence quantity; and
   decision means for deciding type of the target object based on the changing fluorescence quantity.

4. The inspection apparatus according to claim 3, wherein the arithmetic means calculates the changing fluorescence quantity from changing quantity of illumination by the light-emitting device by second order differentiating output data from the light-detecting portion.

5. The inspection apparatus according to claim 3, wherein the decision means decides type of the target object based on a comparison between a pre-determined quantity and the changing fluorescence quantity.

6. An inspection method for inspecting a target object based on content of a fluorescent component included in the target object, the inspection method comprising:
   detecting a start signal;
   calibrating quantity of light emitted from a light-emitting device by outputting an initial control signal to the light-emitting device,
   detecting fluorescence with a light-detecting device while an illuminating member is illuminated by the light emitted by light-emitting device,
   deciding an illumination quantity for the light-emitting device by comparing a pre-determined fluorescence and the fluorescence detected until difference between the pre-determined fluorescence and the fluorescence detected becomes zero, and
   outputting the illumination quantity as a corrected control signal;
   deciding type of the target object based on fluorescence emitted from the target object illuminated by the light emitted by the light-emitting device; and
   continuing deciding the type of the target object until a stop signal is detected.

7. The inspection method according to claim 6, wherein deciding the type of the target object includes:
   changing the control signal, based on the corrected control signal, in an analog manner;
   calculating a second order differential of changing output from the light-detecting device; and
   determining the type of the target object by comparing the second order differential and a pre-determined threshold value.

* * * * *